United States Patent
Yu

(10) Patent No.: US 7,109,334 B2
(45) Date of Patent: Sep. 19, 2006

(54) STEREOSELECTIVE METHODS FOR THE PREPARATION OF NUCLEOSIDES

(75) Inventor: Qing Yu, Laval (CA)

(73) Assignee: Shire BioChem, Inc., Ville Saint-Laurent (CA)

( * ) Notice: Subject to any disclaimer, the term of this patent is extended or adjusted under 35 U.S.C. 154(b) by 0 days.

(21) Appl. No.: 10/170,418

(22) Filed: Jun. 14, 2002

(65) Prior Publication Data

US 2003/0135048 A1    Jul. 17, 2003

Related U.S. Application Data

(60) Provisional application No. 60/298,079, filed on Jun. 15, 2001.

(51) Int. Cl.
C07D 409/04        (2006.01)
C07D 411/04        (2006.01)

(52) U.S. Cl. .................. 544/311; 544/182; 544/198; 544/209; 544/313; 544/314; 544/316; 544/317; 544/318; 546/280.4

(58) Field of Classification Search ............... 544/182, 544/212, 223, 262, 280, 314, 317; 546/117, 546/118, 280.4
See application file for complete search history.

(56) References Cited

U.S. PATENT DOCUMENTS

| | | | |
|---|---|---|---|
| 4,460,767 A | 7/1984 | Matsumura et al. | |
| 5,532,349 A | 7/1996 | Kawauchi et al. | |
| 5,587,480 A | 12/1996 | Belleau et al. | |
| 6,215,004 B1 | 4/2001 | Painter et al. | |

FOREIGN PATENT DOCUMENTS

WO    WO 95/29176    11/1995

OTHER PUBLICATIONS

O'Neill et al, Synlett., 1992, No. 10, pp. 791-792.*
Caputo et al., "A New Strategy for the Asymmetric Synthesis of 1,3-Oxathiolane-Based Nucleoside Analogues", *European Journal of Organic Chemistry*, 1999. pp. 1455-1458.
Belleau et al., "A Novel Class of 1,3-Oxathiolane Nucloside Analogues Having Potent Anti-HIV Activity", *Bioorganic & Medicinal Chemistry Letters*, 1993, vol. 3, No. 8, 1993, pp. 1723-1728.
Chun et al., "Syntheses and Antiviral Activities of 1,3-Dioxolanyl-, 1,3-Oxathiolanyl- and 1,3-Dithiolanylnucleosides with 2-Hydroxymethyl Substituents", *Bioorganic & Medicinal Chemical Letters*, Jun. 1997, vol. 7, No. 11, pp. 1478.
Columbier et al., "Novel Silylating Agents Employing 4-Pentenyl Silyl Ethers", *Tetrahedron Letters*, 1994, vol. 35, No. 44, pp. 8167-8170.
Du et al., "Assymetric Synthesis of Oxazolidine Nucleosides and Related Chemistry", *Nucleosides & Nucleotides*, 1998, 17(1-3), pp. 1-13.
Mansour et al., "Anti-Human Immunodeficiency Virus and Anti-Hepatitis-B Virus Activities and Toxicities of the Enantiomers of 2'-Deoxy-3'-Oxa-4'-Thiocytidine and Their 5-Fluro Analogues In Vitro", *Journal of Medicinal Chemistry*, Jan. 6, 1995, vol. 38, No. 1, pp. 1-4.
Wang et al., "Synthesis of Optically Active 2', 3'-Dideoxy-3'-Oxa-4'-Thio-Ribonucleoside Analogues by Transposition of a Leaving Group on Chiral Oxathiolanes Via a Reductive-Oxidative Process", *Tetrahedron Letters*, 1994, vol. 35, No. 27, pp. 4739-4742.
Nguyen-Ba et al., "Short Synthesis of 2,4-Disubstituted 1,3-Oxathiolane and 1,3-Dithiolane Cytosine Nucleosides: Facile Introduction of a 4-Benzoate Group Using Benzoyl Peroxide", *Synthesis*, May 1998, vol. 5, pp. 759-762.

* cited by examiner

*Primary Examiner*—Thomas C. McKenzie
(74) *Attorney, Agent, or Firm*—Millen, White, Zelano & Branigan, P.C.

(57) ABSTRACT

A process for producing predominantly cis nucleosides or nucleoside analogues and derivatives of formula (A):

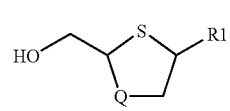

(A)

wherein R1 is a pyrimidine base or a pharmaceutically acceptable derivative thereof and Q is oxygen, carbon or sulphur, comprising a coupling step of the pyrimidine base with a molecule of formula (B) described herein in a suitable coupling solvent, in the presence of catalytic amounts of an element or combination of elements of groups IB or IIB of the periodic table, a tertiary amine and a Lewis acid to obtained an intermediate of formula (D) which is deprotected in the subsequent step to generate the product of formula (A).

27 Claims, No Drawings

STEREOSELECTIVE METHODS FOR THE PREPARATION OF NUCLEOSIDES

This application claims the benefit of priority of U.S. Provisional Application 60/298,079 filed Jun. 15, 2001.

The present invention relates to a novel process for producing cis nucleosides or nucleoside analogues and derivatives of formula (A):

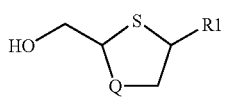
(A)

wherein R1 is a pyrimidine base or a pharmaceutically acceptable derivative thereof and Q is oxygen, carbon or sulphur.

Classes of compounds of formula (A), particularly the 2-substituted 4-substituted 1,3-oxathiolanes have been found to have potent antiviral activity. In particular, these compounds have been found to act as potent inhibitors of HIV-1 replication in T-lymphocytes over a prolonged period of time with less cytotoxic side effects than compounds known in the art (see Belleau et al (1993) Bioorg. Med. Chem. Lett. Vol. 3, No. 8, pp. 1723–1728). These compounds have also been found active against 3TC-resistant HIV strains (see Taylor et al (2000) Antiviral Chem. Chemother. Vol 11, No. 4, pp. 291–301; Stoddart et al (2000) Antimicrob. Agents Chemother. Vol. 44, No. 3, pp. 783–786). These compounds are also useful in prophylaxis and treatment of hepatitis B virus infections.

Methods for the preparation of these compounds have been disclosed in PCT publications WO 92/08717 and WO 95/29176 as well as in publications by Belleau et al (1993) Bioorg. Med. Chem. Lett. Vol. 3, No. 8, pp. 1723–1728; Wang et al (1994) Tetrahedron Lett. Vol. 35, No.27, pp. 4739–4742; Mansour et al , (1995) J. of Med. Chem. Vol. 38, No. 1, pp. 1–4 and Caputo et al in Eur. J. Org. Chem. Vol. 6, pp. 1455–1458 (1999). These processes involve a multitude of steps that increase the cost of production and reduce the yield of the desired compounds.

SUMMARY OF THE INVENTION

The process object of the present invention comprise the step of coupling the intermediate of formula (B):

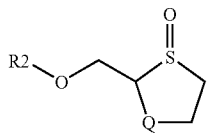
(B)

wherein

R2 is hydrogen or a hydroxyl protecting group such as $C_{7-10}$ arylalkyl, $C_{1-16}$ acyl or $Si(Z^1)(Z^2)(Z^3)$, where $Z^1$, $Z^2$ and $Z^3$ are independently selected from the group consisting of hydrogen; $C_{1-20}$ alkyl optionally substituted by fluoro, bromo, chloro, iodo, $C_{1-6}$ alkoxy or $C_{6-20}$ aryloxy; $C_{7-20}$ aralkyl optionally substituted by halogen, $C_{1-20}$ alkyl or $C_{1-20}$ alkoxy; $C_{6-20}$ aryl optionally substituted by fluoro, bromo, chloro, iodo, $C_{1-20}$ alkyl or $C_{1-20}$ alkoxy; trialkylsilyl; fluoro; bromo; chloro and iodo; and Q is carbon, oxygen or sulfur; with R1, a pyrimidine base or a pharmaceutically acceptable derivative thereof in the presence of a catalytic amount of an element or combination of elements of group IB or IIB, a Lewis acid and a tertiary amine. The resulting intermediate of formula (D)

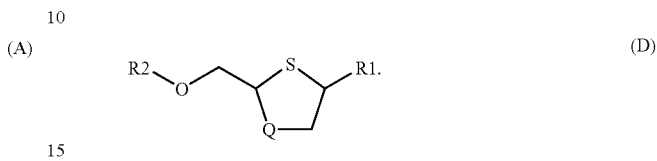
(D)

is deprotected to obtain the cis nucleoside of formula (A):

(A)

The compound of formula (B) may be either:

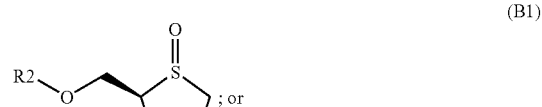
(B1)
; or

(B2)

or a mixture of the two enantiomers.

In an alternative embodiment of the present invention the deprotection of intermediate of formula (D) is achieved by dissolving said intermediate in a suitable solvent in the presence of a deprotection agent.

In an alternative embodiment of the present invention a simple two step preparation method for cis nucleosides of formula (A) wherein the coupling step results in a product wherein the ratio of cis to trans is greater than 2 to 1 is provided.

In a further embodiment the cis to trans ratio of the intermediate product of formula (D) is inversely proportional to the reaction temperature of the coupling step.

In an alternate embodiment of the present invention, the deprotection step results in the selective precipitation of the cis nucleoside of formula (A) by the selection of an appropriate deprotection agent and solvent.

The processes of this invention have the advantages of allowing preparation of a nucleoside of formula (A), analogues or derivatives thereof without using expensive starting materials, cumbersome protection and deprotection steps or addition and removal of 2'- or 3'-substituents.

The process of this invention produces cis nucleosides of formula (A) in high yields, with high purity and high stereoselectivity.

The process of this invention has the further advantage of generating nucleosides whose stereochemical configuration can be easily controlled simply by the selection of the appropriate starting conditions.

DETAILED DESCRIPTION OF THE INVENTION

The present invention discloses a stereoselective process for making predominantly cis nucleosides or nucleoside analogues and derivatives of formula (A):

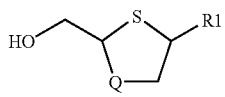

(A)

wherein
R1 is a pyrimidine base or a pharmaceutically acceptable derivative thereof; and
Q is carbon, oxygen or sulfur;
consisting of coupling step of the a compound of formula (B):

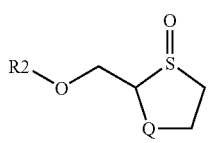

(B)

wherein
R2 is hydrogen or a hydroxyl protecting group such as $C_{7-10}$ aralalkyl, $C_{1-6}$ acyl or $Si(Z^1)(Z^2)(Z^3)$, where $Z^1$, $Z^2$ and $Z^3$ are independently selected from the group consisting of hydrogen; $C_{1-20}$ alkyl optionally substituted by fluoro, bromo, chloro, iodo, $C_{1-6}$ alkoxy or $C_{6-20}$ aryloxy; $C_{7-20}$ aralkyl optionally substituted by halogen, $C_{1-20}$ alkyl or $C_{1-20}$ alkoxy; $C_{6-20}$ aryl optionally substituted by fluoro, bromo, chloro, iodo, $C_{1-20}$ alkyl or $C_{1-20}$ alkoxy; trialkylsilyl; fluoro; bromo; chloro and iodo; with a base R1, wherein R1 is a pyrimidine base or a pharmaceutically acceptable derivative thereof, in a suitable coupling solvent in the presence of a catalytic amount of an element or combination of elements of group IB or IIB ; a tertiary amine and a Lewis acid of formula (C):

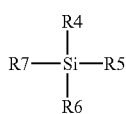

(C)

wherein
R4, R5 and R6 are independently selected from the group consisting of hydrogen; $C_{1-20}$ alkyl optionally substituted by fluoro, bromo, chloro, iodo, $C_{1-6}$ alkoxy or $C_{6-20}$ aryloxy; $C_{7-20}$ aralkyl optionally substituted by halogen, $C_{1-20}$ alkyl or $C_{1-20}$ alkoxy; $C_{6-20}$ aryl optionally substituted by fluoro, bromo, chloro, iodo, $C_{1-20}$ alkyl or $C_{1-20}$ alkoxy; trialkylsilyl; fluoro; bromo; chloro and iodo; and R7 is selected from the group consisting of fluoro; bromo; chloro; iodo; $C_{1-20}$ sulphonate esters, optionally substituted by fluoro, bromo, chloro or iodo; $C_{1-20}$ alkyl esters optionally substituted by fluoro, bromo, chloro or iodo; triiodide; a silyl group of the general formula (R4)(R5)(R6)Si (wherein R4, R5, and R6 are as defined above); $C_{6-20}$ arylselenenyl; $C_{6-20}$ arylsulfenyl; $C_{6-20}$ alkoxyalkyl; and trialkylsiloxy; to yield an intermediate or formula (D):

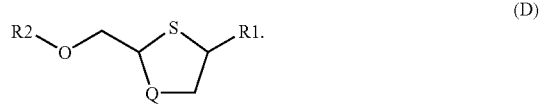

(D)

The coupling step is followed by a deprotection step to yield the cis nucleosides or nucleoside analogues or derivatives of formula (A).

In an alternative embodiment of the present invention a simple two step preparation method for cis nucleosides of formula (A) wherein the process results in a product of formula (A) wherein the ratio of cis to trans is greater than 2 to 1. The invention includes a process wherein the ratio of cis to trans is greater than or equal to 3 to 1.

The term "alkyl", as used herein, unless otherwise specified, refers to a saturated straight, branched, or cyclic, primary, secondary, or tertiary hydrocarbon of $C_{1-30}$, particularly $C_{1-6}$, unsubstituted or optionally mono- or di-substituted by hydroxy, $N_3$, CN, SH, amino, halogen (F, Cl, Br, I), $C_{6-12}$ aryl, $C_{1-6}$ alkyl, $C_{2-12}$ alkoxyalkyl or nitro. It specifically includes methyl, ethyl, cyclopropyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl.

The term "acyl", as used hereinafter refers to a functional group derived from an aliphatic carboxylic acid, by removal of the —OH group of 1 to 30 carbon atoms, particularly 1 to 6 carbon atoms. Like the acid to which it is related, an aliphatic acyl radical may be substituted (by a hydroxy, $N_3$, CN, halogen (F, Cl, Br, I), $C_{6-12}$ aryl, $C_{1-6}$ alkyl, $C_{2-12}$ alkoxyalkyl or nitro) or unsubstituted, and whatever the structure of the rest of the molecule may be, the properties of the functional group remain essentially the same (e.g., acetyl, propionyl, isobutanoyl, pivaloyl, hexanoyl, butyryl, pentanoyl, 3-methylbutyryl, hydrogen succinate, mesylate, valeryl, caproic, caprylic, capric, lauric, myristic, palmitic, stearic, oleic, 3-chlorobenzoate, trifluoroacetyl, chloroacetyl, and cyclohexanoyl ).

The terms "alkenyl" and "alkynyl" represent substituted (by a $N_3$, CN, halogen, hydroxyl or $C_{6-20}$ aryl) or unsubstituted straight, branched or cyclic hydrocarbon chains having 2 to 30 carbon atoms and preferably from 2 to 6 carbon atoms and containing at least one unsaturated group (e.g. allyl).

The term "alkoxy" represents a substituted or unsubstituted alkyl group containing from 1 to 30 carbon atoms and preferably from 1 to 6 carbon atoms, wherein the alkyl group is covalently bonded to an oxygen atom (e.g., methoxy and ethoxy).

The term "aryl" represents a aromatic moiety which may be mono, bi, tri, tetra or penta-substituted by hydroxy, nitro, $N_3$, CN, halogen (F, Cl, Br, I) or combinations thereof and containing at least one benzenoid-type ring, the group may contain from 6 to 14 carbon atoms (e.g., phenyl and naphthyl), particularly 6 to 10 carbon atoms.

The term "aryloxy" represents a substituted (by a halogen, trifluoromethyl or $C_{1-5}$ alkoxy) or unsubstituted aryl moiety, having 6 to 14 carbon atoms, covalently bonded through an oxygen atom (e.g., benzyloxy, phenoxy).

The term "aralalkyl" represents a substituent comprising an aryl moiety attached via an alkyl chain (e.g. benzyl, phenylethyl) wherein the sum total of carbon atoms for the aryl moiety and the alkyl chain is 7 to 21. The aryl or chain portion of the group is optionally mono- or di-substituted with OH, SH, amino, halogen or $C_{1-6}$ alkyl.

The term "thiol" represents $C_{1-6}$ alkyl, $C_{6-15}$ aryl, $C_{7-21}$ aralkyl, $C_{2-6}$ alkenyl or $C_{2-6}$ alkynyl groups covalently bonded to an adjacent sulfur atom bearing a hydrogen.

The terms "alkylthio" (e.g. thiomethy, thioethyl) and "arylthio" (e.g. thiophenyl, thiobenzyl), refers to $C_{1-6}$ alkyl or $C_{6-10}$ aryl groups, unsubstituted or optionally mono- or di-substituted by hydroxy, halogen (F, Cl, Br, I), $C_{6-12}$ aryl, $C_{1-6}$ alkyl, $C_{2-12}$ alkoxyalkyl or nitro, covalently bonded to an adjacent sulfur atom.

The terms "acyloxy" and "alkoxycarbonyl" refer to 1 to 30 carbon atoms chains, particularly 1 to 6 carbon atoms, that are either saturated or unsaturated and may also be straight or branched (e.g.: acetyloxy). The chains may be unsubstituted or optionally mono- or di-substituted by hydroxy, $N_3$, CN, SH, amino, halogen (F, Cl, Br, I), $C_{6-12}$ aryl, $C_{1-6}$ alkyl, $C_{2-12}$ alkoxyalkyl or nitro.

The term "alkoxyalkyl" represents a $C_{1-6}$ alkoxy group attached to an adjacent $C_{1-6}$ alkyl group (e.g., methoxymethyl, ethoxymethyl). They may be unsubstituted or optionally mono- or di-substituted by hydroxy, $N_3$, CN, SH, amino, halogen (F, Cl, Br, I), $C_{6-12}$ aryl, $C_{1-6}$ alkyl, $C_{2-12}$ alkoxyalkyl or nitro.

The term "heterocycle" represents a saturated or unsaturated mono- or polycyclic (i.e. bicyclic) ring incorporating 1 or more (i.e. 1–4) heteroatoms selected from N, O and S. It is understood that a heterocycle is optionally mono- or di-substituted with OH, SH, amino, halogen, $CF_3$, oxo or $C_{1-6}$ alkyl. Examples of suitable monocyclic heterocycles include but are not limited to pyridine, piperidine, pyrazine, piperazine, pyrimidine, imidazole, thiazole, oxazole, furan, pyran and thiophene. Examples of suitable bicyclic heterocycles include but are not limited to indole, benzimidazole, quinoline, isoquinoline, purine, and carbazole.

The term "aralkyl" represents a substituent comprising a $C_{6-10}$ aryl moiety attached via a $C_{1-6}$ alkyl chain (e.g. benzyl, phenethyl). The aryl or chain portion of the group is unsubstituted or optionally mono- or di-substituted by hydroxy, $N_3$, CN, SH, amino, halogen (F, Cl, Br, I), $C_{6-12}$ aryl, $C_{1-6}$ alkyl, $C_{2-12}$ alkoxyalkyl or nitro.

The term "amino" represents $C_{1-6}$ alkyl, $C_{6-10}$ aryl, $C_{2-6}$ alkenyl, $C_{2-6}$ alkynyl, or $C_{7-12}$ aralkyl groups, unsubstituted or optionally mono- or di-substituted by hydroxy, $N_3$, CN, SH, amino, halogen (F, Cl, Br, I), $C_{6-12}$ aryl, $C_{1-6}$ alkyl, $C_{2-12}$ alkoxyalkyl or nitro, wherein the carbon atoms are covalently bonded to an adjacent element through a nitrogen atom (e.g., pyrrolidine). They include primary, secondary and tertiary amines and quaternary ammonium salts.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis. Suitable protecting groups are described, for example, in Greene, et al., "Protective Groups in Organic Synthesis," John Wiley and Sons, Second Edition, 1991, hereby incorporated by reference.

By pyrimidine base derivative or analogue is meant a pyrimidine base found in nucleoside or an analogue thereof which mimics such bases in that their structures (the kinds of atoms and their arrangement) are similar to the normal bases but may possess additional or lack certain of the functional properties of the normal bases. Derivatives of such bases or analogues include those obtained by replacement of a CH moiety by a nitrogen atom (for example, 5-azapyrimidines such as 5-azacytosine) or may have ring substituted by halogen, hydroxyl, azido, cyano, amino, substituted amino, thiol, $C_{1-6}$ alkyl and $C_{6-10}$-aryl.

By the term "pharmaceutically acceptable derivative" of a pyrimidine is meant any pyrimidine base which may give rise to a pharmaceutically acceptable salt, ester, or salt of such ester of a compound of formula (A), or any other compound which, upon administration to the recipient, is capable of providing (directly or indirectly) a compound of formula (A) or an antivirally active metabolite or residue thereof. It will be appreciated by those skilled in the art that the compounds of formula (A) may be modified to provide pharmaceutically acceptable derivatives thereof, at functional groups in the base moiety.

The compound of formula (B) may be either:

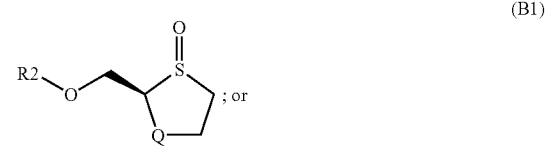

(B1)

(B2)

or a mixture of the two enantiomers. The sulfoxide may be a single enantiomer or a mixture of enantiomers including but not limited to a racemic mixture.

The coupling step of the process object of the present invention includes the addition of one or more elements of group IB or IIB. The element or combination of elements used may be in their oxidized state. This element or combination of elements of group IB or IIB catalyzes the coupling step. The chosen element or combination of elements of group IB or IIB are present in amounts between about 0.25 molar % and about 100 molar %. In another embodiment, the concentration of the element or combination of elements of group IB or IIB may be between about 5% to about 35%.

The process object of the present invention includes a coupling step wherein the element or combination of elements of group IB or IIB are selected from the group comprising $Cu^+$, $Cu^{2+}$, $Ag^+$, $Au^+$, $Au^{3+}$, $Zn^{2+}$ $Cd^{2+}$ and combinations thereof.

The process object of the present invention includes a coupling step wherein the element or combination of elements of group IB or IIB are selected from $Cu^+$, $Cu^{2+}$ or $Zn^{2+}$.

The term tertiary amine includes tertiary amines with high basicity. The tertiary amine is of the form $N(Z^4)(Z^5)(Z^6)$ wherein $(Z^4),(Z^5),(Z^6)$ are independently selected from the group consisting $C_{1-6}$ alkyl optionally substituted with $C_{1-3}$ alkyl, $C_{6-10}$ aryl, halogen. Examples of the tertiary amine include triethylamine, diethylcyclohexylamine, diethylmethylamine, dimethylethylamine, dimethylisopropylamine, dimethylbutylamine, dimethylcyclohexylamine, tributylamine, diethylmethylamine, dimethylisopropylamine and diisopropylethylamine.

The amount of tertiary amine can vary between about 1 eq to about 4 eq. The amount of tertiary amine used may vary between about 1 eq and 2 eq.

The coupling step of the process object of the present invention is preformed in a suitable coupling solvent. A suitable coupling solvent includes $C_{1-10}$ chlorinated organic solvents. Suitable coupling solvents also include $C_{1-8}$ chloroalkyls, $C_{1-8}$ chloroalkenyls, $C_{6-10}$ chloroaryls, $C_{1-8}$ alkylonitriles and combinations thereof. The coupling solvents may be selected from chloromethanes, chloroethanes, methanonitriles or mixtures thereof. The coupling solvents of interest include dichloromethane, chloroform, acetonitrile, dichloroethane, chlorobenzene and combinations thereof.

The amount of coupling solvent used may vary between about 5 mL per g of sulfoxide to 50 mL per gram of sulfoxide. In an alternate embodiment of the invention the amount of coupling solvent is between 10 mL per g of sulfoxide to 30 mL per gram of sulfoxide.

The coupling step of the process object of the present invention is affected by the temperature of the reaction. The cis to trans ratio of the product of formula (D) is inversely proportional to the reaction temperature. The coupling step is preformed at a temperature between about 40 degrees C. and about −50 degrees C. In an alternate embodiment, the coupling step reaction temperature is between about 30 degrees C. and about −40 degrees C.

The second step in the process object of the present invention is a deprotection step. The deprotection crystallization step is preformed in a suitable solvent. Of particular interest are solvents that favor the crystallization of the product of formula (A). Suitable solvents include water, methanol, ethanol, toluene, tert-butyl methyl ether or combinations thereof.

The deprotection may also include the presence of adequate amounts a deprotection agent. Of particular interest are deprotection agents that will aid in the separation of the cis product of formula (A). Suitable deprotection agents are selected according to the identity of the protecting group on the intermediate of formula (D) as shown in Greene, et al., "Protective Groups in Organic Synthesis," John Wiley and Sons, Second Edition, 1991. Deprotection agents may be alkaline. Deprotection agents include sodium hydroxide, sodium methoxide, ammonium hydroxide, potassium hydroxide, lithium hydroxide and methanolic ammonia.

In another embodiment of the present invention, the deprotection agent is present in catalytic amounts. In another embodiment the deprotection agent is present in concentrations between about 0.1 molar percentage and about 50 molar percentage. An alternative embodiment includes deprotection agent concentrations between about 5 to about 20 molar percentage of the deprotection agent.

Conveniently, the base R1 is selected from:

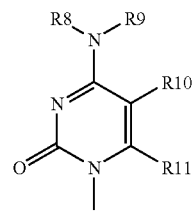

(I)

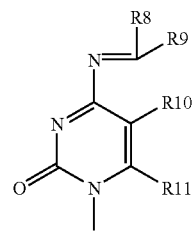

(II)

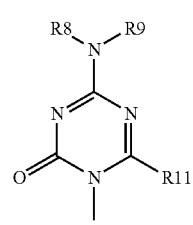

(III)

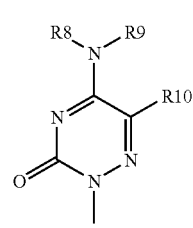

(IV)

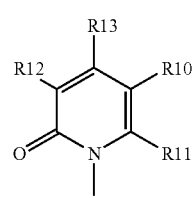

(V)

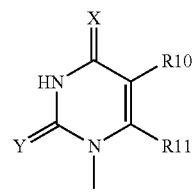

(VI)

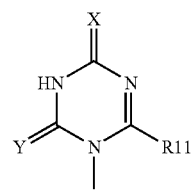

(VII)

-continued

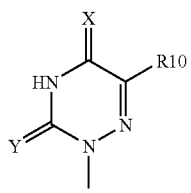

(VIII)

wherein:
x is oxygen, NH or sulfur.
y is oxygen, NH or sulfur.
R8 and R9 are independently selected from hydrogen, hydroxyl, amino, $C_{1-6}$ alkyl or $C_{2-6}$ alkenyl, $C_{2-6}$ alkynyl, $C_{1-10}$ acyl, $C_{6-10}$ aryl, $C_{6-11}$ carbonylaryl, $C_{1-7}$ carbonyloxyalkyl, $C_{6-11}$ carbonyloxyaryl, $C_{2-7}$ carbonylaminoalkyl, or amino acids.
R8 may be a saturated or unsaturated $C_{3-8}$ carbocyclic ring optionally substituted with COOH, C(O)NH$_2$, OH, SH, NH$_2$, NO$_2$, $C_{1-6}$ alkyl, $C_{2-6}$ alkenyl, $C_{2-6}$ alkynyl, halogen, C(O)R14 wherein R14 is a $C_{1-6}$ alkyl, $C_{2-6}$alkenyl, $C_{2-6}$ alkynyl and C(O)OR15 wherein R15 is a $C_{1-6}$ alkyl, $C_{2-6}$ alkenyl, $C_{2-6}$ alkynyl; and R9 is chosen from H, $C_{1-6}$ alkyl, $C_{2-6}$ alkenyl and $C_{2-6}$ alkynyl.
$R_8R_9$ can also be connected to the nitrogen atom to form a saturated or unsaturated $C_{3-8}$ heterocyclic ring optionally substituted with C(O)OH, C(O)NH$_2$, OH, SH, NH$_2$, NO$_2$, $C_{1-6}$ alkyl, $C_{2-6}$ alkenyl, $C_{2-6}$ alkynyl, halogen, C(O)R14 wherein R14 is a $C_{1-6}$ alkyl, $C_{2-6}$ alkenyl, $C_{2-6}$ alkynyl and C(O)OR15 wherein R15 is a $C_{1-6}$ alkyl, $C_{2-6}$ alkenyl, $C_{2-6}$ alkynyl.
R10, R11, R12 and R13 are each independently selected from hydrogen, halogen, hydroxyl, amino, cyano, carboxyl, carbamoyl, $C_{2-7}$ alkoxycarbonyl, hydroxymethyl, trifluoromethyl, $C_{6-10}$ arylthio, $C_{1-6}$ alkyl, $C_{2-6}$ alkenyl substituted or unsubstituted with halogen or azido, $C_{2-6}$ alkynyl, $C_{1-6}$ acyloxy, thiocarboxy, thiocarbamoyl, carbamate, ureido, amidino, or $C_{6-10}$ aryloxy.
In another embodiment of the present invention R1 is

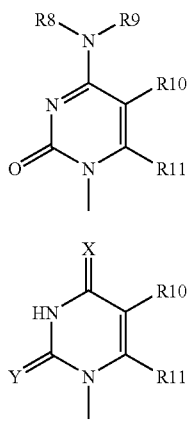

wherein R8 and R9 are independently selected from hydrogen, hydroxyl, amino, $C_{1-10}$ alkyl or $C_{2-10}$ alkenyl, $C_{2-10}$ alkynyl, $C_{1-10}$ acyl, $C_{6-10}$ aryl, $C_{6-16}$ carbonylaryl, $C_{1-10}$ carbonyloxyalkyl, $C_{6-16}$ carbonyloxyaryl, $C_{2-12}$ carbonylaminoalkyl, or amino acids;

R10 and R11 are each independently selected from hydrogen, halogen, hydroxyl, hydroxymethyl, trifluoromethyl, $C_{1-6}$ alkyl, $C_{2-6}$ alkenyl substituted or unsubstituted with halogen, azido, $C_{2-6}$ alkynyl, or $C_{6-10}$ aryloxy; and
X and Y are independently selected from O or S.

In an alternate embodiment R1 is a pyrimidine base selected from N$^4$-alkylpyrimidines, N$^4$-acylpyrimidines, 4-halopyrimidines, N$^4$-acetylenic pyrimidines, 4-amino and N$^4$-acyl pyrimidines, 4-hydroxyalkyl pyrimidines, 4-thioalkyl pyrimidines, thymine, cytosine, 6-azapyrimidine, including 6-azacytosine, 2- and/or 4-mercaptopyrimidine, uracil, C$^5$-alkylpyrimidines, C$^5$-benzylpyrimidines, C$^5$ halopyrimidines, C$^5$-vinylpyrimidine, C$^5$-acetylenic pyrimidine, C$^5$-acyl pyrimidine, C$^5$-amidopyrimidine, C$^5$-cyanopyrimidine, C$^5$-nitropyrimidine, C$^5$-aminopyrimidine, 5-azacytidinyl, 5-azauracilyl, triazolopyridinyl, imidazolopyridinyl, pyrrolopyrimidinyl or pyrazolopyrimidinyl.

The functional oxygen and nitrogen groups on R1 can be protected as necessary or desired. Suitable protecting groups are well known to those skilled in the art, and include trimethylsilyl, dimethylhexylsilyl, t-butyldimethylsilyl, and t-butyldiphenylsilyl, trityl, $C_{1-12}$ alkyl groups, $C_{1-12}$ acyl groups such as acetyl and propionyl, benzoyl, methanesulfonyl, and p-toluenesulfonyl.

In an additional embodiment of the present invention R1 is selected from cytosine, uracil, thymine, 5-fluoropyrimidine or protected analogs of these bases.

Another embodiment of the present invention includes a stereoselective process for making predominantly cis nucleosides or nucleoside analogues and derivatives of formula (A):

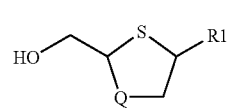

(A)

wherein
R1 is a pyrimidine base selected from N$^4$-alkylpyrimidines, N$^4$-acylpyrimidines, 4-halopyrimidines, N$^4$-acetylenic pyrimidines, 4-amino and N$^4$-acyl pyrimidines, 4-hydroxyalkyl pyrimidines, 4-thioalkyl pyrimidines, thymine, cytosine, 6-azapyrimidine, including 6-azacytosine, 2- and/or 4-mercaptopyrimidine, uracil, C$^5$-alkylpyrimidines, C$^5$-benzylpyrimidines, C$^5$ halopyrimidines, C$^5$-vinylpyrimidine, C$^5$-acetylenic pyrimidine, C$^5$-acyl pyrimidine, C$^5$-amidopyrimidine, C$^5$-cyanopyrimidine, C$^5$-nitropyrimidine, C$^5$-aminopyrimidine, 5-azacytidinyl, 5-azauracilyl, triazolopyridinyl, imidazolopyridinyl, pyrrolopyrimidinyl, pyrazolopyrimidinyl, or a pharmaceutically acceptable derivative thereof; and Q is oxygen, consisting of coupling step of the a compound of formula (B):

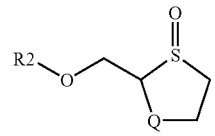

(B)

wherein
- R2 is $C_{7-10}$ aralalkyl, $C_{1-16}$ acyl or $Si(Z^1)(Z^2)(Z^3)$, where $Z^1$, $Z^2$ and $Z^3$ are independently selected from the group consisting of hydrogen; $C_{1-20}$ alkyl optionally substituted by fluoro, bromo, chloro, iodo, $C_{1-6}$ alkoxy or $C_{6-20}$ aryloxy; $C_{7-20}$ aralkyl optionally substituted by halogen, $C_{1-20}$ alkyl or $C_{1-20}$ alkoxy; $C_{6-20}$ aryl optionally substituted by fluoro, bromo, chloro, iodo, $C_{1-20}$ alkyl or $C_{1-20}$ alkoxy; trialkylsilyl; fluoro; bromo; chloro and iodo;

with a base R1, as defined above, in a suitable coupling solvent in the presence of a catalytic amount of an element or combination of elements of group IB or IIB; a tertiary amine and a Lewis acid of formula (C):

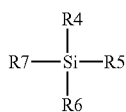

(C)

wherein
- R4, R5 and R6 are independently selected from the group consisting of hydrogen; $C_{1-20}$ alkyl optionally substituted by fluoro, bromo, chloro, iodo, $C_{1-6}$ alkoxy or $C_{6-20}$ aryloxy; $C_{7-20}$ aralkyl optionally substituted by halogen, $C_{1-20}$ alkyl or $C_{1-20}$ alkoxy; $C_{6-20}$ aryl optionally substituted by fluoro, bromo, chloro, iodo, $C_{1-20}$ alkyl or $C_{1-20}$ alkoxy; trialkylsilyl; fluoro; bromo; chloro and iodo; and
- R7 is selected from the group consisting of fluoro; bromo; chloro; iodo; $C_{1-20}$ sulphonate esters, optionally substituted by fluoro, bromo, chloro or iodo; $C_{1-20}$ alkyl esters optionally substituted by fluoro, bromo, chloro or iodo; triiodide; a silyl group of the general formula (R4)(R5)(R6)Si (wherein R4, R5, and R6 are as defined above); $C_{6-20}$ arylselenenyl; $C_{6-20}$ arylsulfenyl; $C_{6-20}$ alkoxyalkyl; and trialkylsiloxy;

to yield an intermediate or formula (D):

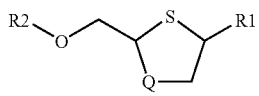

(D)

wherein Q, R1 and R2 are as defined above. The coupling step is followed by a deprotection step wherein said intermediate (D) is dissolved in a suitable solvent in the presence of appropriate amounts of a deprotection agent to yield the cis nucleosides or nucleoside analogues or derivatives of formula (A).

The present invention includes the embodiment wherein the stereoselective process for making predominantly cis nucleosides or nucleoside analogues and derivatives of formula (A):

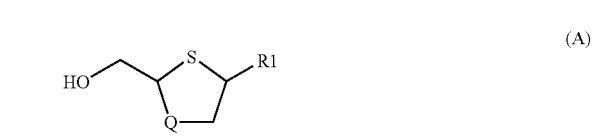

(A)

wherein
- R1 is a pyrimidine base selected from cytosine, uracil, thymine, 5-fluoropyrimidine or a pharmaceutically acceptable derivative thereof; and
- Q is oxygen, consisting of coupling step of the a compound of formula (B):

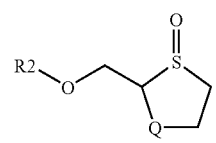

(B)

wherein
R2 is

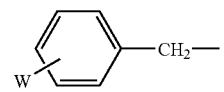

wherein W is halogen, $C_{1-16}$ alkyl, $C_{2-16}$ alkoxyalkyl, $C_{6-10}$ aryl, $C_{1-6}$ alkoxy or nitro; or

wherein E is $C_{6-10}$ aryl, $C_{1-16}$ alkoxy, $C_{2-16}$ alkoxyalkyl or $C_{1-16}$ alkyl; or
$Si(Z^1)(Z^2)(Z^3)$, where $Z^1$, $Z^2$ and $Z^3$ are independently selected from the group consisting of hydrogen; $C_{1-20}$ alkyl optionally substituted by fluoro, bromo, chloro, iodo; $C_{7-10}$ aralalkyl optionally substituted by fluoro, bromo, chloro or iodo; and $C_{6-10}$ aryl optionally substituted by fluoro, bromo, chloro or iodo; with
a base R1, as defined above, in a suitable coupling solvent in the presence of a catalytic amount of Cu or Zn or mixtures thereof; a tertiary amine and a Lewis acid selected from trimethylsilyl triflate bromotrimethylsilane or iodotrimethylsilane; to yield an intermediate or formula (D):

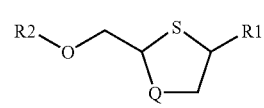

(D)

wherein Q, R1 and R2 are as defined above. The coupling step is followed by a deprotection step wherein said intermediate (D) is dissolved in a suitable solvent in the presence of appropriate amounts of a deprotection agent to yield the cis nucleosides or nucleoside analogues or derivatives of formula (A).

The process object of the present invention includes the reaction scheme shown in Scheme 1:

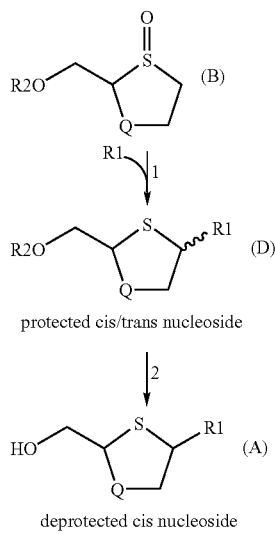

The various steps as illustrated in Scheme 1 may be briefly described as follows:

Step 1: The sulfoxide of formula (B) may be obtained using several methods including those disclosed in PCT publications WO 92/08717 and WO 95/29176, J. Med. Chem. 38(1) 1–4 (1995), Tetrahedron Lett. 35(27) 4739–4742 (1994), Bioorg. Med. Chem. Lett. 3 (8) 1723–1728 (1993) and Eur. J. Org. Chem. 6:1455–1458 (1999). The sulfoxide may be a single enantiomer or a mixture of enantiomers including but not limited to a racemic mixture.

The sulfoxide of formula (B) is coupled with base R1. The base R1 may be previously protected, for example silylated (or silylated in situ) pyrimidine base or pharmaceutically acceptable derivative may be used. The coupling reaction takes place in the presence of a tertiary amine, a Lewis acid of formula (C) and catalytic amounts of an element of groups IB or IIB in a suitable coupling solvent to give the cis/trans pyrimidine nucleoside of formula (D). In the resulting intermediate of formula (D), the cis isomer predominates over the trans isomer in a ratio equal to greater than 2 to 1. The ratio of cis to trans isomer is inversely proportional to the temperature of the reaction temperature. The coupling reaction may be preformed at or below room temperature. The temperature of the coupling step may be between about 0 degrees C and about −50 degrees C.

If a silylated base is used, adequate silylating agent may include t-butyldimethylsilyl triflate 1,1,1,3,3,3 hexamethyldisilazane, TMSI, N,O,bis(TMS) acetonide and trimethylsilyl triflate. Additional protective agents are disclosed in Greene, et al., "Protective Groups in Organic Synthesis," John Wiley and Sons, Second Edition, 1991.

The tertiary amine used in step 1 include triethylamine, diethylcyclohexylamine, diethylmethylamine, dimethylethylamine, dimethylisopropylamine, dimethylbutylamine, dimethylcyclohexylamine, tributylamine, diethylmethylamine, dimethylisopropylamine and diisopropylethylamine and combinations thereof.

The element or combination of elements of groups IB or IIB used in step 1 include Cu, Ag, Au, Zn, or Cd in oxidized state.

The suitable coupling solvent is an organic solvent with one to ten carbons. The suitable coupling solvents include $CH_2Cl_2$, $CH_3CN$ and mixtures thereof.

Suitable Lewis acids include trimethylsilyl triflate bromotrimethylsilane iodotrimethylsilane and combinations thereof. The amount of the Lewis acid may be between about 2 eq to about 5 eq.

Step 2: The cis/trans pyrimidine 1,3-oxathiolane nucleoside of formula (D) is dissolved in a suitable deprotection solvent in the presence of adequate amounts of a deprotection agent to yield the cis nucleosides or nucleoside analogues or derivatives of formula (A). The deprotection step is preformed at a temperature below the boiling point of the suitable deprotection solvent. The reaction temperature of the deprotection step may be between −30 degrees C. and 60 degrees C. The reaction may be preformed at a temperature between about 0 degrees C. to about 35 degrees C.

A deprotection suitable solvent favors the crystallization of the product of formula (A). Suitable solvents include water, methanol, ethanol, toluene, tert-butyl methyl ether or combinations thereof.

Suitable deprotection agents include sodium hydroxide, sodium methoxide, ammonium hydroxide, potassium hydroxide, lithium hydroxide and methanolic ammonia. Of particular interest are deprotection agents which will aid in the separation of the product of formula (A).

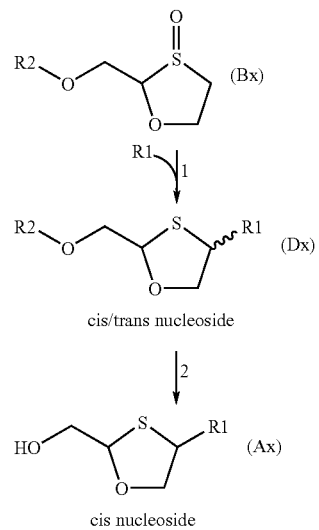

The various steps as illustrated in Schemes 1a may be briefly described as follows:

Step 1: The sulfoxide of the 1,3 oxathiolane of formula (Bx) may be obtained using several methods including those disclosed in PCT publications WO 92/08717 and WO 95/29176, J. Med. Chem. 38(1) 1–4 (1995), Tetrahedron Lett. 35(27) 4739–4742 (1994), Bioorg. Med. Chem. Lett. 3 (8) 1723–1728 (1993). The asymmetric synthesis of the sulfoxide of formula (Bx) is disclosed by Caputo et al in Eur. J. Org. Chem. 6:1455–1458 (1999).

The sulfoxide of the 1,3 oxathiolane of formula (Bx) is coupled with base R1. The base R1 may be previously protected, for example silylated (or silylated in situ) pyrimidine base or pharmaceutically acceptable derivative. The coupling reaction takes place in the presence of a tertiary amine, a Lewis acid of formula (C) and catalytic amounts of an element of groups IB or IIB in a suitable coupling solvent to give the cis/trans pyrimidine 1,3 oxathiolane nucleoside of formula (Dx). In the resulting intermediate of formula (Dx), the cis isomer predominates over the trans isomer in a ratio equal to greater than 2 to 1. The ratio of cis to trans isomer is inversely proportional to the temperature of the reaction temperature. The reaction may be preformed at or below room temperature.

The silylating agent that may be used for the protection of R1 include t-butyldimethylsilyl triflate 1,1,1,3,3,3 hexamethyldisilazane, TMSI, N, O, bis(TMS) acetonite and trimethylsilyl triflate.

The tertiary amine used in step 1 include triethylamine, diethylcyclohexylamine, diethylmethylamine, dimethylethylamine, dimethylisopropylamine, dimethylbutylamine, dimethylcyclohexylamine, tributylamine, diethylmethylamine, dimethylisopropylamine and diisopropylethylamine and combinations thereof.

The element or combination of elements of groups IB or IIB used in step 1 include Cu, Ag, Au, Zn, or Cd in oxidized state.

The suitable coupling solvent is an organic solvent. The suitable coupling solvents include $CH_2Cl_2$, $CH_3CN$ or mixtures thereof.

The Lewis acid that may be used in this step include trimethylsilyl triflate bromotrimethylsilane iodotrimethylsilane and mixtures thereof. The amount of the Lewis acid may be between about 2 eq to about 5 eq.

Step 2: The cis/trans pyrimidine nucleoside of formula (Dx) is dissolved in a suitable deprotection solvent in the presence of adequate amounts of a deprotection agent to yield the cis nucleosides or nucleoside analogues or derivatives of formula (Ax).

A suitable deprotection solvent favors the crystallization of the product of formula (A). Suitable solvents include water, methanol, ethanol, toluene, tert-butyl methyl ether or combinations thereof. Suitable combinations of solvents include methanol and water, methanol and toluene, methanol and tert-butyl methyl ether mixtures.

Suitable deprotection agents include sodium hydroxide, sodium methoxide, ammonium hydroxide, potassium hydroxide, lithium hydroxide and methanolic ammonia. Of particular interest are deprotection agents that will aid in the separation of the product of formula (A).

The deprotection step is preformed at a temperature below the boiling point of the suitable deprotection solvent The following examples illustrate the present invention in a manner of which it can be practiced but, as such, should not be construed as limitations upon the overall scope of the processes of this invention.

1) 2-benzoyloxymethyl-1,3-oxathiolane

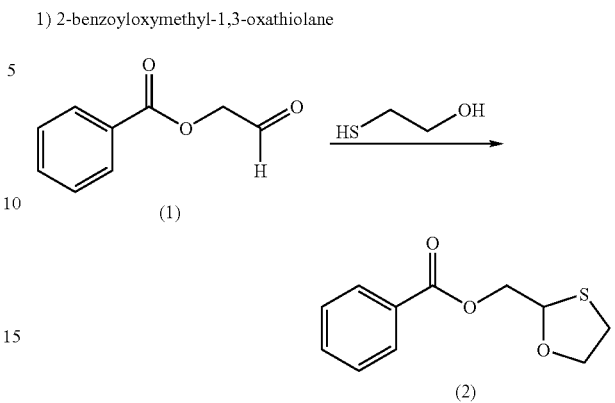

Compound (1) was dissolved in toluene and the solution was heated up to 90–100° C. Catalyst was added followed by mercaptoethanol (portionwise). 5 molar % of catalyst were used. Reactions were carried out on 15 g scale at 0.3M concentration of (1). The reaction mixture was refluxed with water removal by Dean-Stark trap. Results for this step are shown in Table 1.

TABLE 1

| Catalyst | Reaction after 20 min | | Reaction after 40 min | |
| --- | --- | --- | --- | --- |
| | Conversion % | Yield of (2) % | Conversion % | Yield of (2) % |
| $BF_3OEt_2$ | 100 | 79 | 100 | 71 |
| pTsOH | 100 | 82 | 100 | 80 |

Compound (2) was identified by $^1H$- and $^{13}C$-NMR.

$R_f$: 0.39 (hexane: ethyl acetate) $^1H$-NMR: δ (ppm in $CDCl_3$) 8.03 (m, 2H, aromatic) 7.53 (m, 1H, aromatic) 7.39 (m, 2H, aromatic) 5.41 (dd, 1H, $C_2$—H) 4.43 (m, 2H, $C_2$—$CH_2OCC_6H_5$) 4.21 (m, 1H, $C_5$—H) 3.96 (m, 1H, $C_5$—H) 2.98 (m, 2H, $C_4$—H) $^{13}C$-NMR: δ(ppm in $CDCl_3$) 166.82, 133.74, 130.35, 128.97, 83.58, 71.87, 66.62 and 32.74

2) 2-benzoyloxymethyl-1,3-oxathiolane-S-oxide

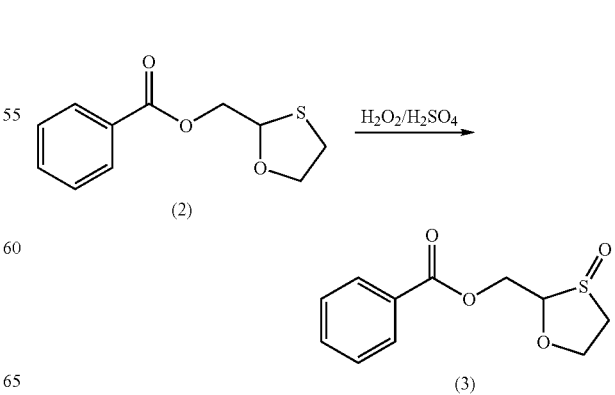

Cold 30% hydrogen peroxide (46 ml, 0.44 mol) was added to (2) (82 g, 0.366 mol) in toluene (8 ml). 10M sulfuric acid (4.5ml, 0.044 mol, 10 mol %) was added dropwise (addition time approximately 1 min). The reaction mixture was vigorously stirred at 25–30° C. for 2 h followed by 1 h string at 30° C. Water (100 ml) was added followed by sodium bicarbonate (3.7 g 0.044 mol) followed by sodium metabisulfite (8 g). Organic layer was separated and aqueous phase was extracted with dichloromethane (3×20 ml). The combined organic extracts were dried over sodium sulfite, concentrated to dryness and triturated with hexane to form a solid. 83 g (94% ) of target compound (3) was obtained.

m.p.: 70–72°
$^1$H-NMR: δ (ppm in CDCl$_3$) 8.05 (m, 2H, aromatic, cis-isomer) 7.95 (m, 2H, aromatic, trans-isomer) 7.56 (m, aromatic) 7.23 (m, aromatic) 4.77 (m, 4H, C$_2$—H, C$_5$—H, and C$_2$—CH$_2$OOCC$_6$H$_5$) 4.43 (m, 1H, C$_5$—H, trans-isomer) 4.09 (m, 1H, C$_5$—H, cis-isomer) 3.11 (m, 2H, C$_4$—H, trans-isomer) 2.75 (m, 2H, C$_4$—H, cis-isomer) $^{13}$C-NMR: δ(ppm in CDCl$_3$) cis-isomer: 166.64, 134.02, 130.42, 129.88, 129.06, 96.16, 68.83, 59.47 and 54.30 trans-isomer: 166.36, 134.12, 130.29, 129.68, 129.15, 108.07, 70.09, 61.83 and 53.47

3) (+/−)-Cis, trans-2benzoylmethyl-4-(N-acetylcytosine-1′-yl)-1,3-oxathiolane

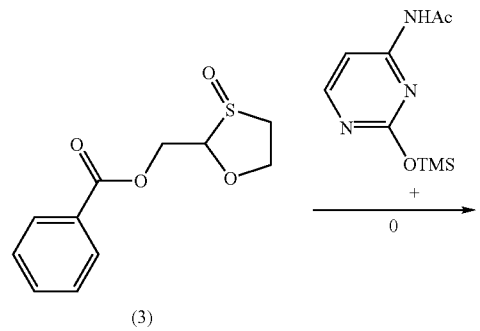

(3)

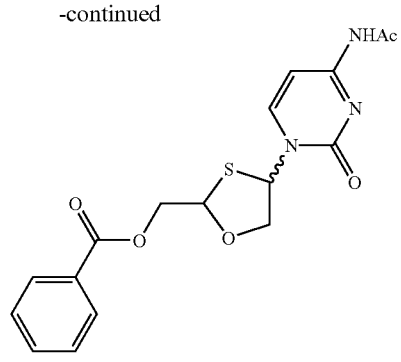

(4)

Compound (3) was dissolved in CH$_2$Cl$_2$ (20 mL/g) and cooled to −15° C. The amine (between 1 and 2 eq) was added followed by addition of TMSI (between 2 and 5 eq) while keeping the internal temperature below −5° C. stirred at −5° C. to −10° C. until the compound (3) disappeared. The CuCl (20%) and the pyrimidine (1.1 eq) was added. The reaction mix was warmed up and kept between 5–10° C. until TLC indicated the reaction is complete. The reaction mixture was poured into 5% NH$_4$OH and stirred for 10 minutes until no solid precipitate was detected. The organic layer was separated and aqueous layer was extracted with CH$_2$Cl$_2$. The organic layer was washed with water, 2% HCl, dilute Na$_2$SO$_3$. The washed organic layer was evaporated to give the product, compound (4). Results for this step are shown in Table 2.

These were characterized by $^1$H and $^{13}$C-NMR. cis-isomer: $^1$H-NMR: δ (ppm in CDCl$_3$) 9.61 (b, 1H, C$_{4'}$—NhCOCH$_3$) 8.29 (d, 1H, C$_{6'}$—H) 8.06 (m, 2H, aromatic) 7.65 (m, 1H, aromatic) 7.51 (m, 2H, aromatic) 7.25 (d, 1H, C$_{5'}$—H) 6.61 (d, 1H, C$_4$—H) 5.50 (t, 1H, C$_2$—H) 4.80 (m, 2H, C$_2$—CH$_2$OOCC$_6$H$_5$) 4.48 (d, 1H, C$_5$—H) 4.05 (dd, 1H, C$_5$—H) 2.25 (s, 3H, CH$_3$) $^{13}$C-NMR: δ (ppm in CDCl$_3$) 170.93, 166.28, 162.80, 155.76, 146.06, 133.91, 129.90, 128.84, 97.45, 85.88, 78.25, 64.60, 63.53 and 24.71. trans-isomer: $^1$H-NMR: δ (ppm in DMSO d$_6$) 10.88 (s, 1H, C$_{4'}$—NhCOCH$_3$) 8.13 (d, 1H, C$_{6'}$—H) 7.96 (m, 2H, aromatic) 7.68 (m, 1H, aromatic) 7.52 (m, 2H, aromatic) 7.20 (d, 1H, C$_{5'}$—H) 6.35 (d, 1H, C$_4$—H) 5.96 (dd, 1H, C$_2$—H) 4.58 (dd, 1H, C$_2$—CH$_2$OOCC$_6$H$_5$) 4.44 (d, 1H, C$_5$—H) 4.29 (m, 2H, C$_5$—H and CH$_2$OOCC$_6$H$_5$) 2.07 (s, 3H, CH$_3$) $^{13}$C-NMR: δ (ppm in DMSO d$_6$) 171.53, 165.84, 162.76, 155.21, 146.59, 134.00, 129.64, 129.23, 96.54, 83.78, 74.24, 64.58, 64.01 and 24.35

TABLE 2

| Pyrimidine | Base | Catalyst (molar eq) | Conditions | Yield (Cis + Trans) | Cis/Trans | Yield % Cis |
|---|---|---|---|---|---|---|
| N—Ac—Cy 1.1eq | DIPEA 1.2eq | | CH$_2$Cl$_2$, −15° C., RT, O/N | 80% | 2.0:1 | 53 |
| N—Ac—Cy 1.1eq | DIPEA 1.2eq | CuCl$_2$ (20%) | CH$_2$Cl$_2$, −15° C., 3 h RT, O/N | 91% | 3.9:1 | 72 |
| N—Ac—Cy 1.1eq | TEA 1.2eq | CuCl$_2$ (20%) | CH$_2$Cl$_2$, −15° C., 5 h RT, O/N | 75% | 3.8:1 | 59 |
| N—Ac—Cy 1.1eq | DMCA 1.2eq | CuCl$_2$ (20%) | CH$_2$Cl$_2$, −15° C., 5 h RT, O/N | 80% | 3.4:1 | 62 |
| N—Ac—Cy 1.1eq | DECA 1.2eq | CuCl$_2$ (20%) | CH$_2$Cl$_2$, −15° C. RT, O/N | 71% | 3.9:1 | 57 |

TABLE 2-continued

| Pyrimidine | Base | Catalyst (molar eq) | Conditions | Yield (Cis + Trans) | Cis/ Trans | Yield % Cis |
|---|---|---|---|---|---|---|
| N—Ac—Cy 1.1eq | DIPEA 1.2eq | CuCl₂ (2%) | CH₂Cl₂, −15° C., 3 h RT, O/N | 80% | 2.4:1 | 56 |
| N—Ac—Cy 1.1eq | DIPEA 1.2eq | CuBr₂ (20%) | CH₂Cl₂, −15° C., 5 h RT, O/N | 80% | 3.7:1 | 63 |
| N—Ac—Cy 1.1eq | DIPEA 1.2eq | Cu(acac)₂ (20%) | CH₂Cl₂, −15° C., 5 h RT, O/N | 85% | 3.7:1 | 67 |
| N—Ac—Cy 1.1eq | DIPEA 1.2eq | CuCl (20%) | CH₂Cl₂, −15° C., 5 h RT, O/N | 80% | 3.6:1 | 63 |
| N—Ac—Cy 1.1eq | DIPEA 1.2eq | CuI (20%) | CH₂Cl₂, −15° C., 5 h RT, O/N | 74% | 3.5:1 | 58 |
| N—Ac—Cy 1.1eq | DIPEA 1.2eq | CuSCN (20%) | CH₂Cl₂, −15° C., 5 h RT, O/N | 70% | 3.1:1 | 53 |
| N—Ac—Cy 1.1eq | DIPEA 1.2eq | ZnBr₂ (20%) | CH₂Cl₂, −15° C., 5 h RT, O/N | 53% | 3.1:1 | 40 |
| Cy 1.1eq | DIPEA 1.2eq | CuCl₂ (20%) | CH₂Cl₂, −15° C., 5 h RT, O/N | 72% | 2.4:1 | 51 |

Cy = cytosine
DIPEA = diisopropylethylamine
TEA = Triethylamine
DECA = diethylcyclohexylamine
DMCA = dimethylcyclohexylamine
Cu(acac)₂ = Copper (II) acetylacetonate 4) 2-hydroxymethyl-4-(cytosin-1′-yl)-1,3-oxathiolane

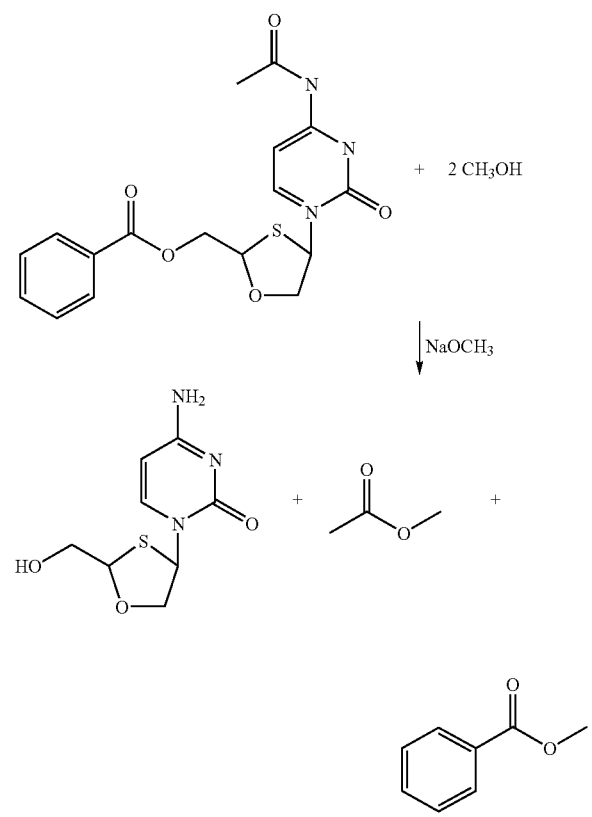

A suspension of the substrate, sodium methoxide, 10 mole percentage, and the appropriate solvent was stirred at RT for 2 h before it was filtered. The filter cake as dried and weighed before checking the C/T ratio (by ¹H NMR) and yield. Results for this step are shown in table 3.

TABLE 3

| Weight of Cis/ Trans mix (g) | Cis/ Trans ratio | Solvent | Strong base | Conditions | % of trans (NMR) | Recovery of Cis (%) |
|---|---|---|---|---|---|---|
| 4 | 3.4:1 | MeOH, | MeONa | Mix and stir at RT | 0 | 89 |
| 10 | 3.4:1 | MeOH | MeONa | Mix and stir at RT | 0 | 88.5 |
| 4 | 3.4:1 | MeOH/ tBME (7:3) | MeONa | Mix and stir at RT | 0 | 90 |
| 25 | 3.4:1 | MeOH/ tBME (7:3) | MeONa | Mix and stir at RT | traces | 91 |
| 1 | 3.4:1 | MeOH/ EtOH (1:1) | MeONa | RT | 0 | 98 |
| 4 | 3.4:1 | MeOH/ EtOH (1:1) | MeONa | Mix and stir at RT | traces | 92.5 |
| 25 | 3.4:1 | MeOH/ EtOH (1:1), 150 mL | MeONa | Mix and stir at RT | traces | 93 |
| 1 | 3.4:1 | MeOH/ Toluene (6:4) | MeONa | RT | traces | 92.5 |
| 4 | 3.4:1 | MeOH: Toluene (6:4) | MeONa | Mix and stir at RT | traces | 90 |
| 25 | 3.4:1 | MeOH/ Toluene (6:4) L | MeONa | Mix and stir at RT | traces | 91 |
| 1 | 3.4:1 | MeOH/ H2O (95:5) | NaOH | RT | 20 | 90 |
| 1 | 3.4:1 | MeOH/ H2O (95:5) | NaOH | At 50° C. | 20 | 90 |

5) Synthiesis of 2benzoylmethyl-4-(N-acetylcytosine-1'-yl)-1,3-oxathiolane using (−) or (+) 2-benzoyloxymethyl-1,3-oxathiolane-S-oxide

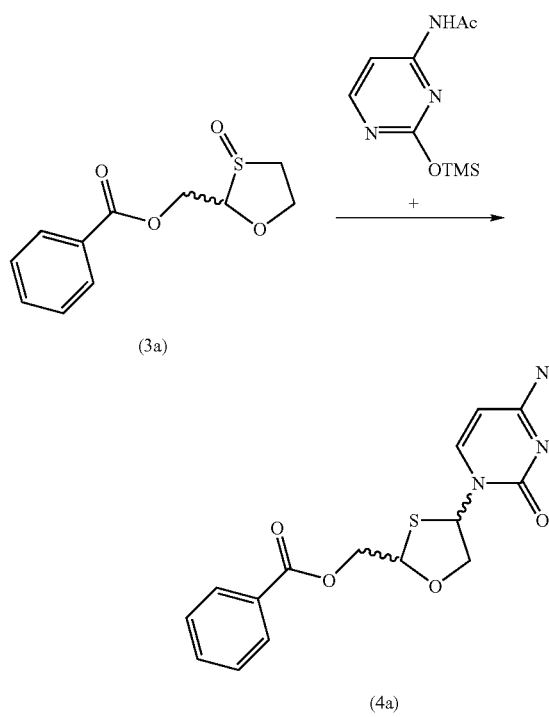

(3a)

(4a)

The enantiomerically pure Compound (3a) was dissolved in CH$_2$Cl$_2$ (10 mL/g) and cooled to reaction temperature. The amine was added followed by addition of TMSI while keeping the internal temperature below −5° C. stirred at −5° C. to −40° C. until the compound (3a) disappeared. The CuCl (20%) and the pyrimidine (1.1 eq) was added. The reaction mix was warmed up and kept between −40 to 30° C. until TLC indicated the reaction is complete. The reaction was cooled to 0° C.-5° C. Celite (12 g, 100% w/w) was added to the suspension and stirred. Concentrated ammonium hydroxyde (was added slowly and the suspension temperature was kept between 0° C.–10° C. Stirred at 0° C.–5° C. The suspension was filtered and the cake was resuspended in dichloromethane. Stirred then filtered. The phases were separated and the aqueous was extracted with dichloromethane. The combined organic layers were washed with a 2% solution of ammonium hydroxyde, water, 2% hydrochloric solution, 2% sodium metabisulfite solution and saturated sodium bicarbonate solution. The organic phase was dried over magnesium sulfate, filtered then reduced in volume in vacuo to give crude base-coupled material as a beige solid. The solids were dissolved in EtOAc and allowed to crystallize. The suspension was stirred at 0–5° C. then filtered. The solids were dried in vacuo to give pure base-coupled product as a pale beige solid. Results for this step are shown in Table 4 and Table 5.

$^1$H NMR (300 MHz)(CDCl$_3$) δ: 2.27 (s, 3H, CH$_3$ cis), 2.29 (s, 3H, CH$_3$ trans), 4.06 (dd, J=4.5 Hz & J=10.8 Hz, 1H, C5 cis), 4.30 (dd, J=3.4 Hz & J=12.4 Hz, 1H, C5 trans), 4.49 (dd, J=3.1 Hz & J=10.8 Hz, 1H, C5 cis) 4.72 (dd, J=8.3 Hz & J=12.4 Hz, 1H, C5 trans), 4.77, (AB, J=4.5 Hz, 2H, CH$_2$OBz cis), 4.84 (AB, J=2.3 Hz, 2H, CH$_2$OBz trans), 5.50 (dd, J=3.1 Hz & J=4.5 Hz, 1H, C4 cis), 5.92 (dd, J=3.4 Hz & J=8.3 Hz 1H, C4 trans), 6.61 (dd, J=2.3 Hz trans & J=4.5 Hz cis, 1H, C2), 7.25 (d, J=7.5 Hz, 1H, C5'), 7.5–8.1 (m, 10H, aromatic cis & trans), 8.30 (d, J=7.5 Hz, 1H, C6'), 9.50 (s 1H, NH). $^{13}$C NMR (300 MHz) (CDCl$_3$) δ: 25.9 (cis & trans), 64.3 (cis), 65.1 (trans), 65.3 (cis & trans), 76.1 (trans), 78.7 (cis), 84.7 (trans), 86.2 (cis), 97.9 (cis), 98.1 (trans), 128.6 (cis & trans), 128.7 (cis & trans), 129.2 (cis & trans), 129.4 (cis & trans), 129.8 (cis & trans), 133.5 (trans), 133.7 (cis), 145.3 (trans), 145.6 (cis), 155.2 (trans), 155.3 (cis), 162.5 (cis & trans), 162.6 (trans), 165.7 (cis), 171.0 (cis), 171.1 (trans).

TABLE 4

| Sulfoxide | Base | Reaction Temp. (° C.) | (−)Cis (%) | (+)Cis (%) | (−)Trans (%) | (+)trans (%) | Cis/Trans (%) |
|---|---|---|---|---|---|---|---|
| BzO—[2-benzoyloxymethyl-1,3-oxathiolane-S-oxide] | DIPEA | −15 | 48.9 | 27.4 | 6.7 | 17 | 3.2:1 |
| BzO—[2-benzoyloxymethyl-1,3-oxathiolane-S-oxide] | TEA | −15 | 70.4 | 5.2 | 1.6 | 22.8 | 3.1:1 |
| BzO—[2-benzoyloxymethyl-1,3-oxathiolane-S-oxide, opposite stereochem] | TEA | −15 | 4.9 | 73.6 | 20 | 1.5 | 3.6:1 |

TABLE 4-continued

| Sulfoxide | Base | Reaction Temp. (° C.) | (−)Cis (%) | (+)Cis (%) | (−)Trans (%) | (+)trans (%) | Cis/Trans (%) |
|---|---|---|---|---|---|---|---|
| BzO—[2-(benzoyloxymethyl)-1,3-oxathiolane S-oxide] | DMCA | −25 | 72.4 | 4.5 | 1.25 | 21.8 | 3.3:1 |
| BzO—[2-(benzoyloxymethyl)-1,3-oxathiolane S-oxide, other stereoisomer] | TEA | −30 (internal temp), warm up to RT after adding silylated base | 1 | 74.4 | 24.6 | 0 | 3:1 |

TABLE 5

| Sulfoxide | Base | Reaction Temperature ° C. | Yield % | Cis/Trans (%) |
|---|---|---|---|---|
| BzO—sulfoxide | TEA + DIPEA | −20 | 74 | 3.3:1 |
| BzO—sulfoxide | (i-pro)NMe₂ | −20 | 72 | 3.7:1 |
| BzO—sulfoxide | TEA | −20 | 63 | 4:1 |
| BzO—sulfoxide | (i-pro)NMe₂ | −20 | 72 | 3.3:1 |
| BzO—sulfoxide | TEA | −20 | 70 | 3.3:1 |

TEA = Triethylamine
DIPEA = Diisopropylethylamine
DMCA = Dimethylcyclohexylamine
(i-pro)NMe$_2$ = Isoproplydimethylamine

The invention claimed is:

1. A stereoselective process for making predominantly cis compounds of formula (A):

(A) HOCH$_2$—[1,3-oxathiolane with R1 substituent, Q in ring]

wherein
R1 is a base selected from:

(I) pyrimidine with R8, R9 on N, R10, R11 substituents (II) pyrimidine with =N—CR8R9, R10, R11 substituents (III) triazine with R8, R9 on N, R11 substituent (IV) triazine with R8, R9 on N, R10 substituent -continued

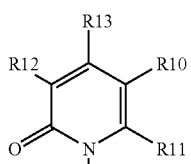
(V)

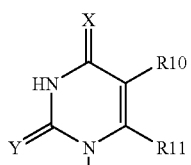
(VI)

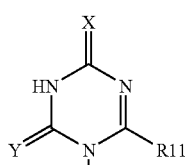
(VII)

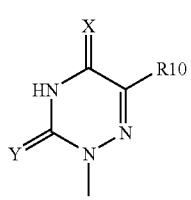
(VIII)

X is oxygen, NH or sulfur;

Y is oxygen, NH or sulfur;

R8 and R9 are independently selected from hydrogen, hydroxyl, amino, $C_{1-6}$ alkyl, $C_{2-6}$ alkenyl, $C_{2-6}$ alkynyl, $C_{1-10}$ acyl, $C_{6-10}$ aryl, $C_{6-11}$ carbonylaryl, $C_{1-7}$ carbonyloxyalkyl, $C_{6-11}$ carbonyloxyaryl, $C_{2-7}$ carbonylaminoalkyl, and amino acids;

R8 can also be a saturated or unsaturated $C_{3-8}$ carbocyclic ring optionally substituted by COOH, C(O)NH$_2$, OH, SH, NH$_2$, NO$_2$, $C_{1-6}$ alkyl, $C_{2-6}$ alkenyl, $C_{2-6}$ alkynyl, halogen, C(O)R14 or C(O)OR15, and R9 H, $C_{1-6}$ alkyl, $C_{2-6}$ alkenyl or $C_{2-6}$ alkynyl;

R8 and R9 can also together be connected to the nitrogen atom to form a saturated or unsaturated $C_{3-8}$ heterocyclic ring optionally substituted by C(O)OH, C(O)NH$_2$, OH, SH, NH$_2$, NO$_2$, $C_{1-6}$ alkyl, $C_{2-6}$ alkenyl, $C_{2-6}$ alkynyl, halogen, C(O)R14 $C_{2-6}$ alkynyl or C(O)OR15;

R14 is $C_{1-6}$ alkyl or $C_{2-6}$ alkenyl;

R15 is $C_{1-6}$ alkyl, $C_{2-6}$ alkenyl, or $C_{2-6}$ alkynyl; and

R10, R11, R12 and R13 are each independently selected from hydrogen, halogen, hydroxyl, amino, cyano, carboxyl, carbamoyl, $C_{2-7}$ alkoxycarbonyl, hydroxymethyl, trifluoromethyl, $C_{6-10}$ arylthio, $C_{1-6}$ alkyl, $C_{2-6}$ alkenyl substituted or unsubstituted with halogen or azido, $C_{2-6}$ alkynyl, $C_{1-6}$ acyloxy, thiocarboxy, thiocarbamoyl, carbamate, ureido, amidino, or $C_{6-10}$ aryloxy; and Q is carbon, oxygen or sulfur;

said process comprising:

coupling a compound of formula (B):

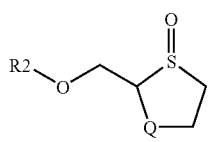
(B)

wherein

R2 is benzoyl, and $Z^1$, $Z^2$ and $Z^3$ are independently selected from hydrogen; $C_{1-20}$ alkyl optionally substituted by fluoro, bromo, chloro, iodo, $C_{1-6}$ alkoxy or $C_{6-20}$ aryloxy; $C_{7-20}$ aralkyl optionally substituted by halogen, $C_{1-20}$ alkyl or $C_{1-20}$ alkoxy; $C_{6-20}$ aryl optionally substituted by fluoro, bromo, chloro, iodo, $C_{1-20}$ alkyl or $C_{1-20}$ alkoxy; trialkylsilyl; fluoro; bromo; chloro and iodo;

with a base R1 in a $C_{1-10}$ coupling solvent in the presence of a catalytic amount of $Cu^+$, $Cu^{2+}$, $Ag^+$, $Au^+$, $Au^{3+}$, $Zn^{2+}$, $Cd^{2+}$ or combinations thereof, in each case being in an oxidized state, a tertiary amine and a Lewis acid to yield an intermediate of formula (D):

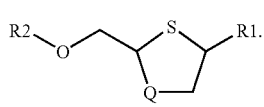
(D)

wherein R1, R2 and Q are defined above; and deprotecting the intermediate of formula (D) to yield the cis compound of formula (A).

2. A process according to claim 1, wherein said Lewis acid is a compound of formula (C):

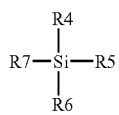
(C)

wherein

R4, R5 and R6 are independently selected from hydrogen; $C_{1-20}$ alkyl optionally substituted by fluoro, bromo, chloro, iodo, $C_{1-6}$ alkoxy or $C_{6-20}$ aryloxy; $C_{7-20}$ aralkyl optionally substituted by halogen, $C_{1-20}$ alkyl or $C_{1-20}$ alkoxy; $C_{6-20}$ aryl optionally substituted by fluoro, bromo, chloro, iodo, $C_{1-20}$ alkyl or $C_{1-20}$ alkoxy; trialkylsilyl; fluoro; bromo; chloro and iodo; and R7 is selected from fluoro; bromo; chloro; iodo; $C_{1-20}$ sulphonate ester; optionally substituted by fluoro, bromo, chloro or iodo; $C_{1-20}$ alkyl esters optionally substituted by fluoro, bromo, chloro or iodo; triiodide; a silyl group of the formula (R4)(R5)(R6)Si; $C_{6-20}$ arylsulfenyl; $C_{6-20}$ arylsulfenyl; $C_{6-20}$ alkoxyalkyl; and trialkylsiloxy.

3. A process according to claim 1, wherein the tertiary amine is of the form N(Z4)(Z5)(Z6) wherein (Z4),(Z5), and (Z6) are independently selected from $C_{1-6}$ alkyl optionally substituted by $C_{1-3}$ alkyl, $C_{6-10}$ aryl or halogen.

4. A process according to claim 1, wherein the organic solvent is a $C_{1-8}$ chloroalkyl, a $C_{1-8}$ chloroalkenyl, a $C_{6-10}$ chloroaryl, $C_{1-8}$ alkylonitrile or mixtures thereof.

5. A process according to claim 4, wherein the organic solvent is selected from chloromethanes, chloroethanes, methanonitriles and mixtures thereof.

6. A process according to claim 3, wherein the tertiary amine is triethylamine, diethylcyclohexylamine, diethylmethylamine, dimethylethylamine, dimethylisopropylamine, dimethylbutylamine, dimethylcyclohexylamine, tributylamine, diethylmethylamine, dimethylisopropylamine, diisopropylethylamine or combinations thereof.

7. A process according to claim 1, wherein Q is oxygen.

8. A process according to claim 1, wherein coupling is preformed at a temperature equal to or less than 30 degrees Celsius.

9. A process according to claim 1, wherein the deprotection step is preformed in the presence of a deprotecting agent and a deprotecting solvent which favors the crystallization of the cis compounds of formula (A).

10. A process according to claim 9, wherein the deprotection agent is alkaline.

11. A process according to claim 10, wherein the deprotection agent is sodium hydroxide, sodium methoxide, ammonium hydroxide, potassium hydroxide, lithium hydroxide, methanolic ammonia or combinations thereof.

12. A process according to claim 9, wherein the deprotecting solvent is water, methanol, ethanol, toluene, tert-butyl methyl ether or combinations thereof.

13. A process according to claim 1, wherein R1 is selected from N4-alkylpyrimidines, N4-acylpyrimidines, 4-halopyrimidines, N4-acetylenic pyrimidines, 4-amino and N4-acyl pyrimidines, 4-hydroxyalkyl pyrimidines, 4-thioalkyl pyrimidines, thymine, cytosine, 6-azapyrimidine, 2- mercaptopyrimidine, 4-mercaptopyrimidine, uracil, C5-alkylpyrimidines, C5-benzylpyrimidines, C5-halopyrimidines, $C_5$-vinylpyrimidine, C5-acetylenic pyrimidine, C5-acyl pyrimidine, C5-amidopyrimidine, C5-cyanopyrimidine, C5-nitropyrimidine, C5-aminopyrimidine, 5-azacytidinyl, and 5-azauracilyl.

14. A stereoselective process for making predominantly cis compounds of formula (A):

wherein
R1 is a base selected from N4-alkylpyrimidines, N4-acylpyrimidines, 4-halopyrimidines, N4-acetylenic pyrimidines, 4-amino and N4-acyl pyrimidines, 4-hydroxyalkyl pyrimidines, 4-thioalkyl pyrimidines, thymine, cytosine, 6-azapyrimidine, including 6-azacytosine, 2- and/or 4-mercaptopyrimidine, uracil, C5 -alkylpyrimidines, C5 -benzylpyrimidines, C5 halopyrimidines, C5 -vinylpyrimidine, C5 -acetylenic pyrimidine, C5 -acyl pyrimidine, C5 -amidopyrimidine, C5 -cyanopyrimidine, C5 -nitropyrimidine, C5 -aminopyrimidine, 5-azacytidinyl, 5-azauracilyl, triazolopyridinyl, imidazolopyridinyl, pyrrolopyrimidinyl, and pyrazolopyrimidinyl; and Q is oxygen;
said process comprising coupling a compound of formula (B):

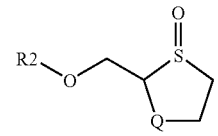

wherein
R2 is benzoyl, and
Z1, Z2 and Z3 are independently selected from hydrogen; $C_{1-20}$ alkyl optionally substituted by fluoro, bromo, chloro, iodo, $C_{1-6}$ alkoxy or $C_{6-20}$ aryloxy; $C_{7-20}$ aralkyl optionally substituted by halogen, $C_{1-20}$ alkyl or $C_{1-20}$ alkoxy; $C_{6-20}$ aryl optionally substituted by fluoro, bromo, chloro, iodo $C_{1-20}$ alkyl or $C_{1-20}$ alkoxy; trialkylsilyl; fluoro; bromo; chloro and iodo;
with a base R1 in a coupling solvent in the presence of a catalytic amount of $Cu^+$, $Cu^{2+}$, $Ag^+$, $Au^+$, $Au^{3+}$, $Zn^{2+}$, $Cd^{2+}$ or combinations thereof, in each case being in an oxidized state, a tertiary amine and a Lewis acid of formula (C):

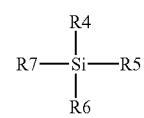

wherein
R4, R5 and R6 are independently selected from hydrogen; $C_{1-20}$ alkyl optionally substituted by fluoro, bromo, chloro, iodo, $C_{1-6}$ alkoxy or $C_{6-20}$ aryloxy; $C_{7-20}$ aralkyl optionally substituted by halogen, $C_{1-20}$ alkyl or $C_{1-20}$ alkoxy; $C_{6-20}$ aryl optionally substituted by fluoro, bromo, chloro, iodo, $C_{1-20}$ alkyl or $C_{1-20}$ alkoxy; trialkylsilyl; fluoro; bromo; chloro and iodo; and
R7 is selected from fluoro; bromo; chloro; iodo; $C_{1-20}$ sulphonate esters optionally substituted by fluoro, bromo, chloro or iodo; $C_{1-20}$ alkyl esters optionally substituted by fluoro, bromo, chloro or iodo; triiodide; a silyl group of the formula (R4)(R5)(R6)Si; $C_{6-20}$ arylselenenyl; $C_{6-20}$ arylsulfenyl; $C_{6-20}$ alkoxyalkyl; and trialkylsiloxy;
to yield an intermediate of formula (D):

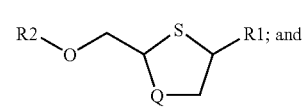

deprotecting intermediate D wherein said intermediate (D) is dissolved in a solvent which favors the crystallization of the cis compounds of formula (A) in the presence of an appropriate amounts of a deprotection agent to yield the cis compounds of formula (A).

15. A process according to claim 1, wherein R1 is a base selected from cytosine, uracil, thymine, and 5fluoropyrimidine.

16. A process according to claim 1, wherein said catalytic amount of $Cu^+$, $Cu^{2+}$, $Ag^+$, $Au^+$, $Au^{3+}$, $Zn^{2+}$, $Cd^{2+}$ or combinations thereof, is 0.25 molar % to 100 molar %.

17. A process according to claim 1, wherein said coupling is performed in the presence of a catalytic amount of $Cu^+$, $Cu^{2+}$ or $Zn^{2+}$.

18. A process according to claim 1, wherein the amount of tertiary amine is 1 eq to 4 eq.

19. A process according to claim 1, wherein the amount of coupling solvent used is 5 mL per g of sulfoxide to 50 mL per gram of sulfoxide.

20. A process according to claim 19, wherein the amount of coupling solvent is between 10 mL per g of sulfoxide to 30 mL per gram of sulfoxide.

21. A process according to claim 1, wherein the coupling step is preformed at a temperature of 40 degrees C. to −50 degrees C.

22. A process according to claim 1, wherein the coupling step is preformed at a temperature of 30 degrees C. to −40 degrees C.

23. A process according to claim 1, wherein deprotection is preformed in a solvent selected from water, methanol, ethanol, toluene, tert-butyl methyl ether and combinations thereof.

24. A process according to claim 1, wherein the amount of deprotection agent is 0.1 molar percentage to 50 molar percentage.

25. A process according to claim 24, wherein the amount of deprotection agent is 5 to about 20 molar percentage of the deprotection agent.

26. A process according to claim 24, wherein if functional oxygen and nitrogen groups are present on R1 they are protected using protecting selected from trimethylsilyl, dimethylhexylsilyl, t-butyldimethylsilyl, and t-butyldiphenylsilyl, trityl, $C_{1-12}$ alkyl groups, and $C_{1-12}$ acyl.

27. A process according to claim 1, wherein said coupling is performed in the presence of a catalytic amount of $CuCl_2$, CuCl, CuBr, CuI, CuSCN, $ZnBr_2$, Cu(II)acetylacetonate or combinations thereof.

* * * * *

UNITED STATES PATENT AND TRADEMARK OFFICE
CERTIFICATE OF CORRECTION

PATENT NO.       : 7,109,334 B2                                     Page 1 of 1
APPLICATION NO.  : 10/170418
DATED            : September 19, 2006
INVENTOR(S)      : Qing Yu It is certified that error appears in the above-identified patent and that said Letters Patent is hereby corrected as shown below:

Column 25, line 53, reads "C(O)R14 $C_{2-6}$ alkynyl" should read -- C(O)R14, $C_{2-6}$ alkynyl --
Column 26, line 24, reads "$Cd^{2+}$or" should read -- $Cd^{2+}$ or --
Column 26, line 58, reads "sulphonate ester;" should read -- sulphonate esters --
Column 26, line 62, reads "arylsulfenyl; $C_{6-20}$ arylsulfenyl" should read
-- arylselenenyl; $C_{6-20}$ arylsulfenyl --
Column 27, line 9-10, reads "dietnylmethylamine," should read
-- diethylmethylamine, --
Column 27, line 16, reads "preformed" should read -- performed --
Column 27, line 20, reads "preformed" should read -- performed --
Column 28, line 21, reads "iodo $C_{1-20}$ alkyl" should read -- iodo, $C_{1-20}$ alkyl --
Column 28, line 60, reads "intermediate D" should read -- intermediate (D) --
Column 28, line 63, reads "appropriate amounts" should read -- appropriate amount --
Column 28, line 66-67, reads "5fluoropyrimidine." should read
-- 5-fluoropyrimidine. --
Column 29, line 16, reads "preformed" should read -- performed --
Column 29, line 19, reads "preformed" should read -- performed --
Column 30, line 2, reads "preformed" should read -- performed --

Signed and Sealed this

Seventh Day of July, 2009

JOHN DOLL
*Acting Director of the United States Patent and Trademark Office*